United States Patent
Jang et al.

(10) Patent No.: US 11,629,112 B2
(45) Date of Patent: Apr. 18, 2023

(54) METHOD FOR PREPARATION OF 1,4-CYCLOHEXANEDIMETHANOL

(71) Applicant: HANWHA SOLUTIONS CORPORATION, Seoul (KR)

(72) Inventors: Namjin Jang, Daejeon (KR); Eun Jeong Kim, Daejeon (KR); Sun Uk Lee, Daejeon (KR); Jong Kwon Lee, Daejeon (KR)

( * ) Notice: Subject to any disclaimer, the term of this patent is extended or adjusted under 35 U.S.C. 154(b) by 0 days.

(21) Appl. No.: 17/293,482

(22) PCT Filed: Dec. 16, 2019

(86) PCT No.: PCT/KR2019/018516
§ 371 (c)(1),
(2) Date: May 13, 2021

(87) PCT Pub. No.: WO2020/138973
PCT Pub. Date: Jul. 2, 2020

(65) Prior Publication Data
US 2022/0127212 A1 Apr. 28, 2022

(30) Foreign Application Priority Data
Dec. 27, 2018 (KR) ........................ 10-2018-0171228

(51) Int. Cl.
| C07C 51/36 | (2006.01) |
| C07C 51/353 | (2006.01) |
| C07C 29/149 | (2006.01) |
| C07C 29/158 | (2006.01) |
| C07C 29/56 | (2006.01) |
| B01J 21/06 | (2006.01) |
| B01J 23/44 | (2006.01) |
| B01J 23/62 | (2006.01) |

(52) U.S. Cl.
CPC .......... *C07C 29/158* (2013.01); *C07C 29/149* (2013.01); *C07C 29/56* (2013.01); *C07C 51/353* (2013.01); *C07C 51/36* (2013.01); *B01J 21/066* (2013.01); *B01J 23/44* (2013.01); *B01J 23/626* (2013.01)

(58) Field of Classification Search
CPC .... C07C 51/347; C07C 67/333; C07C 67/293
See application file for complete search history.

(56) References Cited

U.S. PATENT DOCUMENTS

| 5,231,218 A | 7/1993 | Summer |
| 2005/0014973 A1 | 1/2005 | Endou |
| 2008/0051600 A1 | 2/2008 | Hiroshi |
| 2015/0183699 A1* | 7/2015 | Hembre et al. ........ C07C 29/177 |
| 2017/0107164 A1 | 4/2017 | Choi |

FOREIGN PATENT DOCUMENTS

| CN | 103539660 A * | 1/2014 | ........ C07C 51/353 |
| CN | 103539660 A | 1/2014 | |
| EP | 3118181 A1 | 1/2017 | |
| JP | 58-024540 A | 2/1983 | |
| JP | 3549885 B2 | 3/1996 | |
| JP | H08-502747 A | 3/1996 | |
| JP | 2000-080053 A | 3/2000 | |
| JP | 2000191602 A | 7/2000 | |
| JP | 2001-151716 A | 6/2001 | |
| JP | 2002-060356 A | 2/2002 | |
| JP | 2002145824 A | 5/2002 | |
| JP | 2014177422 A | 9/2014 | |
| JP | 2015054828 A * | 3/2015 | ........ C07C 29/151 |
| JP | 2018076282 A | 5/2018 | |
| KR | 19990064411 A | 8/1999 | |
| KR | 100943872 B1 | 6/2004 | |
| KR | 20040047974 A | 6/2004 | |
| KR | 1020150002258 A | 1/2015 | |
| KR | 20150062911 A | 6/2015 | |
| KR | 1020160056208 | 5/2016 | |
| KR | 20190063107 | 7/2019 | |
| KR | 20190081123 A | 7/2019 | |
| KR | 20190142121 | 12/2019 | |
| WO | 2015156582 A1 | 10/2015 | |
| WO | 2019-240393 A1 | 12/2019 | |

OTHER PUBLICATIONS

Machine translation CN103539660A, pp. 1-4 (Year: 2014).*
Machine translation JP2015054828A, pp. 1-14 (Year: 2015).*
Machine translation of patent No. JP2000191602A, pp. 1-9 (Year: 2000).*
Hadjiivanov, K. et al. "Surface Chemistry of Titania (Anatase) and Titania-supported Catalysts" Chemical Society Reviews, 1996, pp. 61-69 (Year: 1996).*
Bazhenov, A. S. et al. "Understanding Structure and Stability of Monoclinic Zirconia Surfaces from First-Principles Calculations" Top Catal (2017) 60:382-391; Published Sep. 15, 2016 (Year: 2016).*
International Search Report dated Apr. 17, 2020.
JP Office Action dated Jun. 27, 2022.
Adolf Baeyer: "Ueber Die Constitution Des Benzols", Justus Liebigs Annalen Der Chemie, Verlag Chemie GMBH, DE, vol. 245, No. 1-2, 1888, pp. 103-190, xp002630849.

* cited by examiner

Primary Examiner — Medhanit W Bahta
(74) Attorney, Agent, or Firm — Harvest IP Law LLP

(57) ABSTRACT

The present disclosure relates to a method for preparation of 1,4-cyclohexanedimethanol. According to the present disclosure, two step reduction reactions are conducted using terephthalic acid as starting material, and an isomerization process for increasing the rate of trans isomers of CHDA is introduced therebetween, thereby providing a method capable of stably preparing CHDM with high rate of trans isomers.

12 Claims, 2 Drawing Sheets

[FIG. 1]
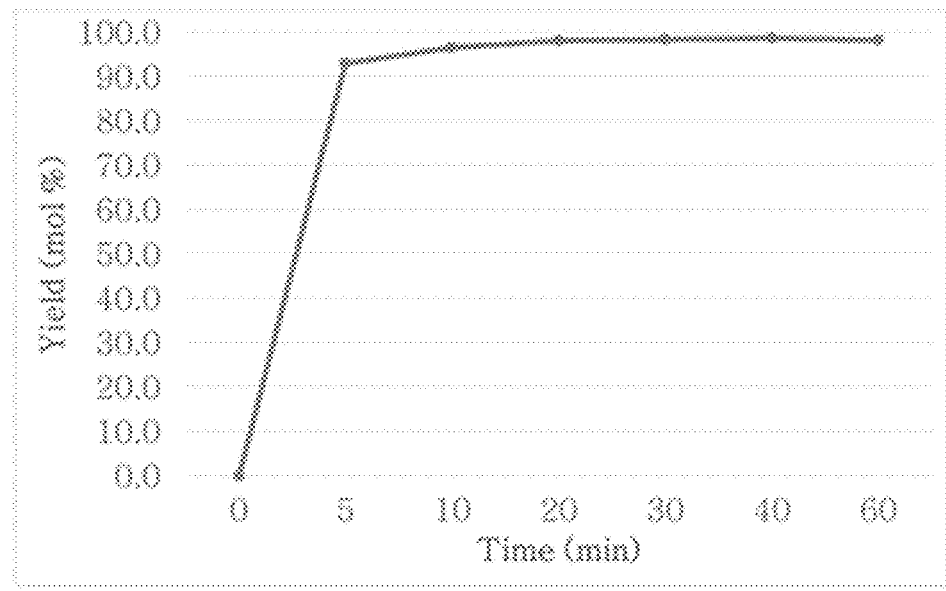
[FIG. 2]
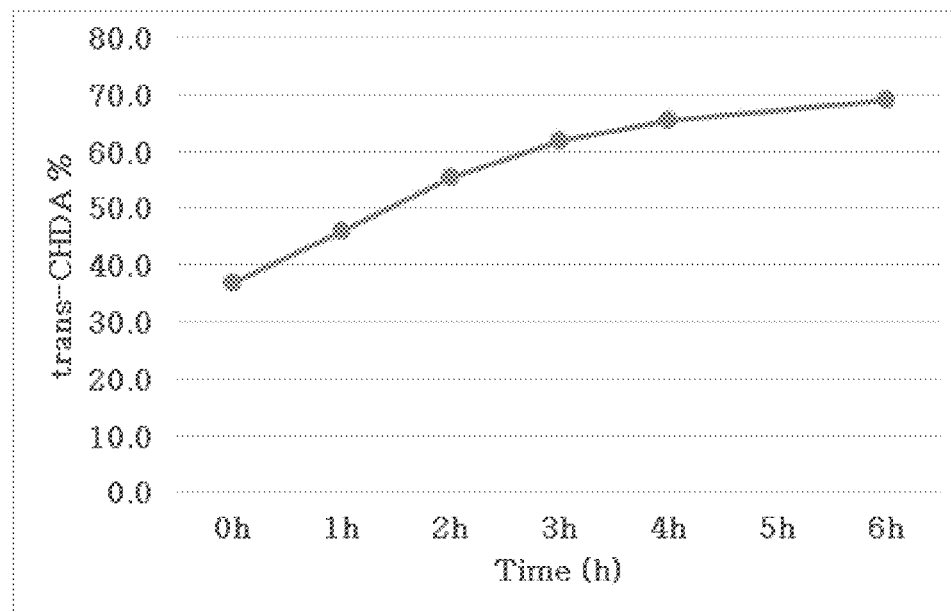

[FIG. 3]
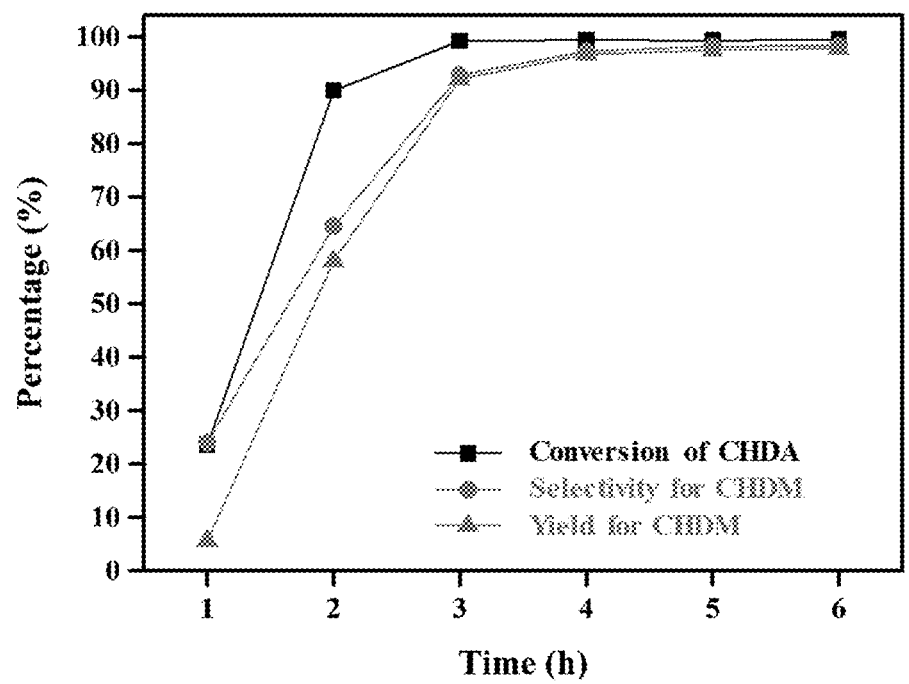

METHOD FOR PREPARATION OF 1,4-CYCLOHEXANEDIMETHANOL

CROSS-REFERENCE TO RELATED APPLICATION(S)

This application is a National Stage of International Application No. PCT/KR2019/018516 filed Dec. 26, 2019, claiming priority based on Korean Patent Application No. 10-2018-0171228 filed Dec. 27, 2018 with the Korean Intellectual Property Office, the disclosures of which are herein incorporated by reference in their entirety.

BACKGROUND OF THE INVENTION

(a) Field of the Invention

This invention relates to a method for preparation of 1,4-cyclohexanedimethanol.

(b) Description of the Related Art 1,4-cyclohexanedimethanol (1,4-cyclohexanedimethanol, CHDM) is widely used as the raw material of medicine, synthetic resin, synthetic fiber or dye, and the like, and particularly, is used as the raw material of environment-friendly polyester polyethylene terephthalate.

1,4-cyclohexanedimethanol exists as cis and trans stereoisomers, and for higher quality product, it is required to have higher rate of trans 1,4-cyclohexanedimethanol (trans CHDM) than cis CHDM.

Among the preparation methods of 1,4-cyclohexanedimethanol, a method by the hydrogenation reaction of dimethyl terephthalate (DMT) is commercially used a lot. This is a method wherein phthalate is reacted with methanol to prepare DMT, and then, 1,4-cyclohexanedimethanol is produced by two step hydrogenation reactions. The first hydrogenation reaction converts DMT into DMCD (diester dimethyl 1,4-cyclohexanedicarboxylate), and the second hydrogenation reaction converts DMCD into CHDM. Wherein, the rate of cis CHDM and trans CHDM is determined according to the kind of a catalyst. In case a copper chromite catalyst, which is industrially mainly used copper chrome oxide, is used, CHDM is prepared at a rate of cis CHDM and trans CHDM of about 3:7. Since this method uses DMT, and uses a trans esterification reaction using methanol, reaction and separation processes are complicated, and additives should be used for isomerization so that the quality of the final product may be influenced.

Other methods include a method wherein phthalate is first hydrogenated and converted into 1,4-cyclohexanedicarboxylic acid (CHDA), and CHDA is hydrogenated and converted into CHDM. This method uses a heterogeneous catalyst and consists of two step hydrogenation reactions.

Korean Laid-Open Patent Publication No. 2015-0062911 suggested a method of preparing CHDM by two step reduction processes of phthalate. However, this method does not pass through an isomerization reaction, and the rate of trans CHDM is low.

And, WO 2015-156582 suggested a method of preparing CHDM using a single reactor in a fixed bed reactor using a composite metal catalyst composition. According to this method, the rate of trans CHDM is also low, and since temperature control and gradient of phthalate and an intermediate product CHDA in the fixed bed reactor are not constant, there is a high probability of crystallization in the middle, thus deteriorating catalyst performance.

Korean Registered Patent No. 0943872 suggested a method of separately producing an intermediate product trans CHDA to increase trans CHDM rate. This is a method wherein trans CHDA is produced in a solid or molten state, simultaneously with progressing an isomerization reaction using melting point difference of cis CHDA and trans CHDA. However, this method required a process of removing water used as a solvent, or other solvents, and is operated at low temperature for recrystallization, and thus, heat used in the reduction process of phthalate should be removed. Thus, it may not be economical.

And, as another method, Japanese Laid-Open Patent Publication No. 2014-177422 suggested a method of obtaining desired trans CHDM rate by controlling hydrogenation reaction temperature and time. This is a method of simultaneously progressing an isomerization reaction simultaneously with a reduction reaction of CHDA, and controlling reaction temperature and reaction time in the fixed bed reactor, but in the fixed bed reactor, during conversion of reactant CHDA, it is easily crystallized, and thereby, catalyst performance decreases, and thus, desired yield and trans CHDM rate cannot be achieved.

(Patent Document 1) Korean Laid-Open Patent Publication No. 2015-0062911
(Patent Document 2) WO2015-156582
(Patent Document 3) Korean Registered Patent No. 0943872
(Patent Document 4) Japanese Laid-Open Patent Publication No. 2014-177422

SUMMARY OF THE INVENTION

This invention was made to solve the above problems, and it is an object of the invention to provide a method for stably preparing CHDM with high rate of trans isomers, by conducting two step reduction reactions using terephthalic acid as starting material, and introducing an isomerization process for increasing the rate of trans isomers of CHDA therebetween.

In order to solve the problems, one aspect of the invention provides a method for preparation of 1,4-cyclohexanedimethanol, comprising steps of:

conducting a hydrogenation reaction of terephthalic acid in the presence of a first hydrogenation catalyst to prepare 1,4-cyclohexanedicarboxylic acid (CHDA) comprising cis isomers and trans isomers;

conducting an isomerization reaction of the reaction product of the step 1 in the presence of an isomerization catalyst to isomerizes at least a part of the cis isomers of CHDA into trans isomers; and conducting a hydrogenation reaction of the reaction product of the step 2 in the presence of a second hydrogenation catalyst to prepare 1,4-cyclohexanedimethanol (CHDM) comprising cis isomers and trans isomers.

According to the preparation method of 1,4-cyclohexanedimethanol of the present disclosure, by continuous hydrogenation reaction and isomerization reaction using terephthalic acid as starting material, CHDM can be prepared with high yield, and CHDM with high rate of trans isomers among the cis isomers and trans isomers of CHDM can be stably prepared.

And, according to the preparation method of the present disclosure, an isomerization process is conducted using the hydrogenation reaction product of terephthalic acid without additional purification or separation, thus simplifying the process, and the isomerization step can be conducted while maintaining the reaction temperature in the hydrogenation reaction step of terephthalic acid, and thus, heat energy loss is not generated and the process may be economical.

BRIEF DESCRIPTION OF THE DRAWINGS

FIG. 1 is a graph showing CHDA yield according to time, in the hydrogenation reaction of terephthalic acid.

FIG. 2 is a graph showing trans CHDA rate according to isomerization reaction time.

FIG. 3 is a graph showing changes in CHDM yield, conversion, and selectivity according to time, in the hydrogenation reaction of CHDA.

DETAILED DESCRIPTION OF THE EMBODIMENTS

The terms used herein are only to explain specific embodiments and are not intended to limit the invention. A singular expression includes a plural expression thereof, unless it is expressly stated or obvious from the context that such is not intended. As used herein, the terms "comprise" or "have", etc. are intended to designate the existence of practiced characteristic, number, step, constructional element or combinations thereof, and they are not intended to preclude the possibility of existence or addition of one or more other characteristics, numbers, steps, constructional elements or combinations thereof.

Although various modifications can be made to the invention and the invention may have various forms, specific examples will be illustrated and explained in detail below. However, it should be understood that these are not intended to limit the invention to specific disclosure, and that the invention includes all the modifications, equivalents or replacements thereof without departing from the spirit and technical scope of the invention.

Hereinafter, a method for preparation of 1,4-cyclohexanedimethanol according to specific embodiments of the invention will be explained in more detail.

The method for preparation of 1,4-cyclohexanedimethanol of the present disclosure comprises steps of: conducting a hydrogenation reaction of terephthalic acid in the presence of a first hydrogenation catalyst to prepare 1,4-cyclohexanedicarboxylic acid (CHDA) comprising cis isomers and trans isomers; conducting an isomerization reaction of the reaction product of the step 1 in the presence of an isomerization catalyst to isomerizes at least a part of the cis isomers of CHDA into trans isomers; and conducting a hydrogenation reaction of the reaction product of the step 2 in the presence of a second hydrogenation catalyst to prepare 1,4-cyclohexanedimethanol (CHDM) comprising cis isomers and trans isomers.

As such, the method for preparation of 1,4-cyclohexanedimethanol can stably prepare CHDM with high trans isomer rate, by conducting two step hydrogenation (reduction) reactions using terephthalic acid as starting material, and introducing an isomerization process for increasing the rate of trans isomers of CHDA therebetween.

Thus, according to the method for preparation of 1,4-cyclohexanedimethanol of the present disclosure, CHDM can be prepared with high yield, and CHDM with high rate of trans isomers among the cis isomers and trans isomers of CHDM can be prepared.

Hereinafter, a method for preparation of 1,4-cyclohexanedimethanol according to one embodiment of the invention will be explained in detail according to each step.

Step 1

The step 1 is a step wherein a hydrogenation reaction of terephthalic acid is conducted in the presence of a first hydrogenation catalyst, to prepare 1,4-cyclohexanedicarboxylic acid (CHDA) comprising cis isomers and trans isomers.

By the hydrogenation reaction of step 1, the aromatic ring of terephthalic acid is hydrogenated, and thus, terephthalic acid is converted into corresponding 1,4-cyclohexane dicarboxylic acid.

As explained, in case a hydrogenation reaction of terephthalic acid is conducted in the presence of a first hydrogenation catalyst, CHDA, the reaction product of the step 1, is obtained in the form of mixture of cis isomers and trans isomers, namely, cis CHDA and trans CHDA, and the mole ratio of cis isomers and trans isomers is about 8:2 to about 6:4, and cis isomers are obtained more. And, the mole ratio of cis CHDA to trans CHDA appears to be within the above range, regardless of the kind of a hydrogenation catalyst or detailed conditions of a hydrogenation reaction.

In case CHDA prepared by the hydrogenation reaction of terephthalic acid is subjected to a hydrogenation reaction again to prepare CHDM, the mole ratio of cis isomers and trans isomers is maintained as it is and does not significantly changes, and thus, in order to increase the rate of trans isomers of CHDM, a method of separating only trans CHDA and conducting a hydrogenation reaction, or progressing an isomerization reaction simultaneously with the hydrogenation reaction of CHDA has been suggested. However, by these previous methods, it is difficult to simultaneously achieve high yield and high trans CHDM rate, and the process is too complicated or a production cost is high, and thus, it is not industrially preferable.

Thus, according to the preparation method of the present disclosure, a CHDA product with high cis isomer rate is first subjected to an isomerization reaction under specific conditions to relatively increase the rate of trans isomers compared to cis isomers, and CHDA with relatively increased rate of trans isomers is subjected to a hydrogenation reaction, thereby simultaneously improving the total yield of CHDM and the rate of trans CHDM by continuous and simplified process.

Meanwhile, the hydrogenation process of step 1 may be conducted in a liquid phase or gas phase. According to one embodiment of the invention, the hydrogenation reaction may be progressed while the terephthalic acid is liquid dissolved in a solvent such as water and hydrogen is a gaseous state, Meanwhile, in order to minimize side reactions and optimize rate of reactants to improve process productivity, the amount of hydrogen introduced into a reactor may be 3 moles or more, or 4 moles or more, or 7 moles or more, and 300 moles or less, or 100 moles or less, or 50 moles or less, or 30 moles or less, based on 1 mole of terephthalic acid.

If the amount of hydrogen is less than 3 moles based on 1 mole of terephthalic acid, reaction conversion rate may decrease, and thus, conversion rate of 95% or more cannot be obtained, and if it is greater than 300 moles, the residence time of liquid drops of liquid raw materials in the reactor may be shortened due to hydrogen, and thus, conversion rate may decrease, by-products may increase, or catalyst life may rapidly decrease. Thus, the amount of hydrogen is preferably within the above range.

Although the temperature and pressure conditions of gas and liquid raw materials introduced in the reactor are not specifically limited in the present disclosure, gas raw material may be adjusted to a pressure of about 100 to about 200 bar, preferably about 130 to about 160 bar and a temperature of about 100 to about 200° C., preferably about 130 to about 180° C., and liquid raw material may be adjusted to a pressure of about 100 to about 200 bar, preferably about 130 to about 160 bar and a temperature of about 100 to about 300° C., preferably about 210 to about 260° C.

As the first hydrogenation catalyst, catalyst known to be usable in the hydrogenation reaction of terephthalic acid may be used.

According to one embodiment of the present disclosure, the first hydrogenation catalyst may comprise one or more metals selected from the group consisting of palladium(Pd), rhodium(Rh), ruthenium(Ru), and platinum(Pt) as an active ingredient.

Preferably, the first hydrogenation catalyst may comprise palladium(Pd) as an active ingredient.

According to one embodiment of the invention, the amount of the active ingredient of the first hydrogenation catalyst used may be appropriately controlled according to the content of reactant terephthalic acid. Specifically, as the content of the first hydrogenation catalyst based on terephthalic acid is higher, a reaction rate increase, and thus, the first hydrogenation catalyst may be added in such an amount that the weight ratio of the first hydrogenation catalyst to terephthalic acid may become 0.01:1 or more.

However, if the content of the first hydrogenation catalyst based on terephthalic acid is beyond a certain level, reaction rate increasing effect may be insignificant compared to the amount used, and thus, reaction efficiency may decrease. Thus, the first hydrogenation catalyst may be more specifically added in such an amount that the weight ratio of the first hydrogenation catalyst to terephthalic acid may become 0.01:1 to 3:1, or 0.01:1 to 2.5:1, or 0.1:1 to 2:1.

However, the above weight ratio does not limit the range of the present disclosure, and the rate of the catalyst may be appropriately controlled according to detailed reaction conditions and the kind of a reactor.

The first hydrogenation catalyst may be used while being supported in a carrier, wherein as the carrier, those known in the art may be used without limitations. Specifically, carriers such as carbon, zirconia ($ZrO_2$), titania ($TiO_2$), alumina ($Al_2O_3$), or silica ($SiO_2$), and the like may be used.

When carbon is used as the carrier, although not specifically limited, at least one selected from the group consisting of active carbon, carbon black, graphite, graphene, OMC (ordered mesoporous carbon) and carbon nanotube may be used.

In case the first hydrogenation catalyst is supported in a carrier, the amount of the active ingredient of the first hydrogenation catalyst may be preferably 20 parts by weight or less, and may be 15 parts by weight or less, or 10 parts by weight or less, and 1 part by weight or more, or 3 parts by weight or more, based on 100 parts by weight of the carrier. If the amount of the first hydrogenation catalyst is too large based on 100 parts by weight of the carrier, a reaction may rapidly progress on the surface of the catalyst, and during this process, side reactions may also increase and the amount of by-products may rapidly increase, and if it is too small, yield of hydrogenation reaction may decrease, and thus, the above range is preferable.

In the present disclosure, the hydrogenation reaction conditions in step 1 are not specifically limited, but for example, the reaction pressure may be 50 bar or more, or 80 bar or more, or 100 bar or more, and 220 bar or less, or 200 bar or less, or 180 bar or less. If the reaction pressure is less than 50 bar, a reaction may not sufficiently occur, and thus, an excessive amount of a catalyst may be consumed, and residence time may too lengthen to increase by-products, and if it is greater than 200 bar, excessive energy such as electric power may be required during process operation, and manufacture cost of facilities such as reactor may significantly increase, and thus, the above range is preferable.

And, the reaction temperature may be 100° C. or more, or 150° C. or more, or 200° C. or more, and 300° C. or less, or 280° C. or less, or 260° C. or less. If the reaction temperature is less than 100° C., a reaction rate may be too slow and a reaction may not be smooth, and if it is greater than 300° C., by-products may rapidly increase, and catalyst life may be influenced, and thus, the above range is preferable.

And, during the hydrogenation reaction, a stirring process may be also conducted, and through the control of speed during the stirring process, hydrogenation reaction efficiency may be increased. Specifically, the stirring process may be conducted at a speed of 500 to 2,000 rpm, and more specifically, it is preferable that the stirring may be conducted at 700 to 1,500 rpm or 700 to 1,000 rpm.

Meanwhile, the stirring process may be conducted using a common stirrer used in gas-liquid reactions.

It may be more preferable in terms of process efficiency that the process may be conducted for 1 to 10 hours under conditions fulfilling all the above hydrogenation reaction conditions.

The reaction product obtained after step 1 comprises CHDA comprising cis isomers and trans isomers, solvent water, a catalyst, and the like, which are used as reactants of the isomerization reaction of step 2 described below. If necessary, the catalyst included in the reaction product may be removed by a catalyst filter, and the like, and then, the reaction product may be sent as a reactant of the isomerization reaction of step 2.

According to one embodiment of the invention, based on the total weight of the reaction product of step 1, the weight of CHDA comprising cis isomers and trans isomers may be 0.1 to 10 wt %, or 10 to 20 wt %.

Step 2

The step 2 is a step wherein an isomerization reaction of the reaction product of the step 1 is conducted to in the presence of an isomerization catalyst to isomerize at least a part of the cis isomers of CHDA into trans isomers.

During the isomerization reaction, through the reaction mechanism in which cis isomers of CHDA are adsorbed to the isomerization catalyst, and an isomerization reaction is progressed, and then, the product is desorbed, isomerization into trans CHDA is progressed.

The isomerization catalyst used in the isomerization step may comprise one or oxides of Group 4 transition metal such as zirconium(Zr), titanium(Ti), or hafnium(Hf).

Since the Group 4 transition metal oxide exhibits excellent interaction with cis CHDA compared to inorganic oxides such as silica, ceria, and the like, it may exhibit excellent reaction efficiency during the isomerization reaction of CHDA.

And, unlike transition metal oxide such as alumina, magnesia, and the like, it exhibits appropriate adsorption and desorption respectively for reactant and product during an isomerization reaction, and thus, there is no concern about the product trans CHDA being strongly adsorbed to the isomerization catalyst without separation after completing the isomerization reaction and decreasing the yield. And, in case the isomerization catalyst is surface treated or modified so as to have functional groups as before, adsorption of reactant and desorption of product may be influenced, and thus, isomerization reaction efficiency may be deteriorated, or yield may decrease, but in the present disclosure, the isomerization catalyst is non-surface treated or non-modified, thus exhibiting appropriate adsorption and desorption.

As specific examples of the isomerization catalyst that can be used in the present disclosure, zirconia or titania, and the like may be mentioned, and among them, one or mixture of two or more may be used.

Zirconia has high melting point and thus excellent fire resistance, and it is chemically very stable. Thus, during the isomerization reaction, there is no concern about generation of side reactions. And, since it exhibits sufficient interactions with reactant, it may exhibit more excellent catalytic effect for CHDA isomerization. Zirconia may have various crystal structures such as monoclinic system, tetragonal system or hexagonal system, and considering thermal/chemical stability and catalytic effect for CHDA isomerization, it may be more preferable to have monoclinic system.

And, titania has excellent chemical, material stability, and exhibits sufficient interactions with reactant, thereby exhibiting more excellent catalytic effect during CHDA isomerization. Titania may have crystal structures of anatase, rutile and brookite, and considering easiness of catalyst preparation and catalytic effect for CHDA isomerization, it may be more preferable to have an anatase crystal structure.

According to one embodiment of the invention, the amount of the isomerization catalyst used may be appropriately controlled according to the content of reactant CHDA. Specifically, as the content of the isomerization catalyst based on CHDA is higher, a reaction rate increases, and thus, in the isomerization method of CHDA according to one embodiment of the invention, the isomerization catalyst may be added in such an amount that the weight ratio of the isomerization catalyst to CHDA may become 0.1:1 or more.

However, in case the content of the isomerization catalyst based on CHDA is beyond a certain level, the effect of increasing reaction rate compared to the amount used may be insignificant, and reaction efficiency may decrease. Thus, the isomerization catalyst may be added in such an amount that the weight ratio of the isomerization catalyst to CHDA may become 0.1:1 to 5:1.

Considering the effect of reaction rate improvement according to the control of the weight ratio of the isomerization catalyst to CHDA, and the effect of trans CHDA yield increase, the isomerization catalyst may be more preferably added in such an amount that the weight ratio of the isomerization catalyst to CHDA may become 0.1:1 to 5:1, or 0.1:1 to 4:1, or 0.2:1 to 3:1.

However, the above weight ratio does not limit the scope of the present disclosure, and the rate of the catalyst may be appropriately controlled according to detailed reaction conditions and the kind of a reactor.

Meanwhile, the reaction product of step 1, which is the subject of an isomerization step, has higher rate of cis isomers than trans isomers as explained above, and for example, the mole ratio of cis CHDA to trans CHDA is about 8:2 to about 6:4. The reaction product of step 1 may comprise water used as a solvent in step 1, in addition to CHDA.

According to the preparation method of the present disclosure, in the isomerization reaction of step 2, the reaction product of step 1 is used as reactant as it is without additional purification or separation of CHDA, thus simplifying the process, and the reaction of step 2 may be conducted while maintaining the reaction temperature in step 1, and thus, heat energy loss is not generated, and it is economically very favorable.

By the isomerization reaction of step 2, at least a part of the cis isomers of CHDA are isomerized into trans isomers.

More specifically, among 100 mol % of cis isomers of CHDA, 50 mol % or more, or 60 mol % or more, or 70 mol % or more, and 99 mol % or less, or 90 mol % or less may be converted into trans isomers.

Thus, compared to the reaction product of step 1, in the reaction product of step 2 obtained after the isomerization reaction, the rate of cis isomers and trans isomers of CHDA is reversed, and for example, the mole ratio of cis isomers and trans isomers of CHDA may be 4:6 to 2:8.

During the isomerization reaction of step 2, the reaction temperature may be 100° C. or more, or 150° C. or more, or 200° C. or more, and 300° C. or less, or 280° C. or less, or 260° C. or less, similarly to step 1. If the reaction temperature is less than 100° C., the reaction rate may be too slow and the reaction may not be smooth, and if it is greater than 300° C., by-products may rapidly increase. And, catalyst life may also be influenced, and thus, the above range is preferable.

Meanwhile, as explained above, the isomerization reaction of step 2 may be conducted while maintaining the reaction temperature in step 1, and thus, additional heating may not be required, but if necessary, additional heating process for compensating heat loss to the outside or heat removal process for removing reaction heat of the isomerization reaction may be conducted.

In the present disclosure, the isomerization reaction conditions of step 2 are not specifically limited, but for example, the reaction pressure may be 20 bar or more, or 30 bar or more, or 40 bar or more, and 200 bar or less, or 150 bar or less, or 120 bar or less. If the reaction pressure is less than 20 bar, reactions may not sufficiently occur, and thus, an excessive amount of catalyst may be consumed, and a residence time may too lengthen, and thus, by-products may increase, and if it is greater than 200 bar, excessive energy may be required during process operation, and manufacture cost of facilities such as a reactor may significantly increase. Thus, the above range is preferable.

And, during the isomerization reaction, a stirring process may be conducted, and through the control of the speed of the stirring process, reaction efficiency during the isomerization reaction may be increased. Specifically, the stirring process may be conducted at a speed of 500 to 2,000 rpm, and more specifically, it may be preferably conducted at a speed of 700 to 1,300 rpm or 800 to 1,200 rpm.

Meanwhile, the stirring process may be conducted using a common stirrer.

It is more preferable in terms of process efficiency that the process is conducted for 1 to 10 hours under conditions fulfilling all the above isomerization reaction conditions.

Step 3

The step 3 is a step wherein the reaction product of step 2 is reduced in the presence of a second hydrogenation catalyst to prepare 1,4-cyclohexanedimethanol (CHDM) comprising cis isomers and trans isomers.

More specifically, the step 3 is a step wherein CHDA having higher trans isomer rate than cis isomer rate, which is the product produced through the hydrogenation reaction of step 1 and the isomerization reaction of step 2, is subjected to a hydrogenation reaction, thereby reducing the carboxylic groups of CHDA to prepare 1,4-cyclohexanedimethanol (CHDM).

According to one embodiment of the invention, the second hydrogenation catalyst may comprise, as active ingredients, one or more metals selected from the group consisting of palladium(Pd), rhodium(Rh), ruthenium(Ru), and platinum(Pt), and one or more metals selected from the group consisting of tin(Sn), iron(Fe), rhenium(Re), and gallium(Ga).

Preferably, as the active ingredients of the second hydrogenation catalyst, ruthenium(Ru) and tin(Sn) may be included.

According to one embodiment of the invention, the amount of the active ingredients of the second hydrogenation catalyst may be appropriately controlled according to the content of the reactant CHDA. Specifically, as the content of the isomerization catalyst based on CHDA increases, a reaction rate increases, and thus, in the CHDA isomerization method according to one embodiment of the invention, the second hydrogenation catalyst may be added in such an amount that the weight ratio of the second hydrogenation catalyst to CHDA may become 0.01:1 or more.

However, if the content of the second hydrogenation catalyst based on CHDA is beyond a certain level, the effect of increasing reaction rate compared to the amount used may be insignificant, and reaction efficiency may decrease, and thus, the second hydrogenation catalyst may be more specifically added in such an amount that the weight ratio of the active ingredients of the second hydrogenation catalyst to CHDA may become 0.01:1 to 3:1.

Considering the effect of reaction rate improvement according to the control of the weight ratio of the second hydrogenation catalyst to CHDA, the second hydrogenation catalyst may be more preferably added in such an amount that the weight ratio of the second hydrogenation catalyst to CHDA may become 0.01:1 to 3:1, or 0.1:1 to 3:1, or 0.1:1 to 2:1 or 0.5:1 to 2:1.

However, the above weight ratio does not limit the scope of the present disclosure, and the rate of catalyst may be appropriately controlled according to detailed reaction conditions, and the kind of a reactor.

Such a second hydrogenation catalyst may be used while being supported in a carrier, wherein as the carrier, those known in the art may be used without limitations. Specifically, carriers such as carbon, zirconia ($ZrO_2$), titania ($TiO_2$), alumina ($Al_2O_3$), or silica ($SiO_2$), and the like may be used.

According to one embodiment of the invention, in case ruthenium(Ru) and tin(Sn) are included as the active ingredients of the second hydrogenation catalyst, ruthenium(Ru) and tin(Sn) may be included respectively in an amount of 1 to 20 parts by weight, or 1 to 10 parts by weight, or 3 to 8 parts by weight, based on 100 parts by weight of the total carrier.

When carbon is used as the carrier, although not specifically limited, at least one selected from the group consisting of active carbon, carbon black, graphite, graphene, OMC (ordered mesoporous carbon) and carbon nanotube may be used.

Preferably, it may be carbon black having high mesopore rate in the total pores, and for example, the active carbon may be SXULTRA, CGSP, PK1-3, SX 1G, DRACO S51HF, CA-1, A-51, GAS 1240 PLUS, KBG, CASP and SX PLUS, and the like, and the carbon black may be BLACK PEARLS®, ELFTEX®, VULCAN®, MOGUL®, MONARCH®, EMPEROR®, and REGAL®, and the like, but not limited thereto.

Wherein, according to the present disclosure, in the carbon carrier, the volume rate of mesopores having pore size of 2 to 50 nm in the total pores may be 50% or more. Preferably, in the carbon carrier, the volume rate of mesopores in the total pores may be 70% or more, and more preferably 75% or more.

Wherein, if the volume rate of mesopores is less than 50%, there may be problems in terms of microscopic material transfer speed of reactant and product in the carbon carrier, and if the average size of the pores is greater than 50 nm, physical strength of the carrier may be weak, and thus, the above ranges are preferable.

And, according to the present disclosure, the carbon comprises ordered mesoporous carbon (OMC) having specific surface area (BET) of 100 to 1,500 $m^2/g$. Preferably, the carbon may comprise ordered mesoporous carbon (OMC) having specific surface area (BET) of 200 to 1,000 $m^2/g$. Wherein, if the specific surface area of carbon is less than 100 $m^2/g$, it may be difficult for active metals (Ru, Sn) to be highly dispersed, and if the specific surface area of carbon is greater than 1,500 $m^2/g$, the rate of mesopores may decrease, and thus, the above range is preferable.

And, according to circumstances, the carbon carrier of the catalyst according to the present disclosure may comprise micropores in an appropriate rate, besides mesopores, and preferably, it may comprise 0 to 25 vol % of micropores based on the total pores. Wherein, if the volume rate of the micropores is greater than 25%, there may be a problem in terms of microscopic material transfer speed of reactant and product in the carbon carrier, and thus, the above range is preferable.

Although the hydrogenation reaction conditions of step 3 are not specifically limited in the present disclosure, for example, the reaction pressure may be 50 bar or more, or 80 bar or more, or 100 bar or more, and 220 bar or less, or 200 bar or less, or 180 bar or less. If the reaction pressure is less than 50 bar, reactions may not sufficiently occur, and thus, an excessive amount of a catalyst may be consumed, and a residence time may too lengthen, thus increasing by-products, and if it is greater than 200 bar, excessive energy may be required during process operation, and manufacture cost of facilities such as a reactor may significantly increase, and thus, the above range is preferable.

And, the reaction temperature may be 100° C. or more, or 150° C. or more, or 200° C. or more, and 300° C. or less, or 280° C. or less, or 260° C. or less. If the reaction temperature is less than 100° C., a reaction rate may be too slow and a reaction may not smoothly occur, and if it is greater than 300° C., by-products may rapidly increase, and catalyst life may be influenced, and thus, the above range is preferable.

And, during the hydrogenation reaction, a stirring process may be also conducted, and through the control of speed during the stirring process, hydrogenation reaction efficiency may be increased. Specifically, the stirring process may be conducted at a speed of 500 to 2,000 rpm, and more specifically, it is preferable that the stirring may be conducted at 700 to 1,500 rpm or 700 to 1,000 rpm.

Meanwhile, the stirring process may be conducted using a common stirrer

It may be more preferable in terms of process efficiency that the process may be conducted for 1 to 10 hours under conditions fulfilling all the above hydrogenation reaction conditions.

Since in the hydrogenation reaction of step 3, the mole ratio of cis isomers to trans isomers of CHDA is maintained as it is, obtained CHDM also has higher trans isomer rate than cis isomer rate. Namely, in the product of step 3, the mole ratio of cis isomers to trans isomers of CHDM may be 4:6 to 2:8.

Thus, CHDM finally obtained by the preparation method of the present disclosure may be usefully used as the raw material for the preparation of higher quality products.

Hereinafter, the invention will be explained in more detail with reference to the following examples. However, these examples are presented to illustrate the invention, and the scope of the invention is not limited thereby.

EXAMPLE

Example 1

Step 1

As a reactor, a batch reactor capable of withstanding at 300° C., 150 bar was prepared. Into the batch reactor, 1.5 g of reactant terephthalic acid (TPA). 1 g of 5 wt % hydrogenation catalyst Pd/C, and 250 g of solvent distilled water were introduced, and the atmosphere in the reactor was replaced with nitrogen, and then, while stirring at 50 rpm, the temperature of the mixed solution was raised to 250° C.

After the temperature of the mixed solution reached 250° C., it was stirred for 30 minutes to dissolve TPA while maintaining the temperature. And then, hydrogen pressure of 120 bar was filled in the reactor, a stirring speed was increased to 800 rpm, and a hydrogenation reaction was conducted for 1 hour while stirring.

After the reaction was completed, a product comprising 1.47 g of CHDA (mole ratio of cis CHDA:trans CHDA=6.5: 3.5), and 250 g of water was obtained. The reaction product of the step 1 was used for step 2 reaction without purification. The yield of CHDA according to hydrogenation reaction time was shown in FIG. 1.

Referring to FIG. 1, after a hydrogenation reaction for 1 hour, CHDA was obtained with the final yield of 98%, conversion of 99%, and selectivity of 99%.

Step 2

As a reactor, a batch reactor capable of withstanding at 300° C., 150 bar was prepared. Into the batch reactor, 4.05 g of the reaction product of step 1, 1.125 g of zirconia (monoclinic system), and 250 g of solvent distilled water were introduced, and while stirring at 50 rpm, the temperature of the mixed solution was raised to 230° C. (concentration of CHDA in the solution:1.6 wt %, weight ratio of zirconia/CHDA=0.28). After the temperature of the mixed solution reached 230° C., the stirring speed was increased to 1000 rpm, and it was reacted for 6 hours while stirring.

After the reaction was completed, a product comprising 4 g of CHDA (cis CHDA:trans CHDA=3:7), and 250 g of water was obtained. The reaction product of step 2 was used for step 3 reaction without purification.

The rate of trans CHDA according to isomerization reaction time was shown in FIG. 2.

Referring to FIG. 2, it can be confirmed that the rate of trans CHDA was about 35% in the initial reactant, but after an isomerization reaction for 6 hours, the rate of trans CHDA increased to about 70%. The rate of trans CHDA and cis CHDA was confirmed by gas chromatography.

Step 3

As a reactor, a batch reactor capable of withstanding at 300° C., 150 bar was prepared. The batch reactor is an apparatus capable of stirring for reactions, in which nitrogen for purging and hydrogen for hydrogenation were introduced. Into the batch reactor, 4.05 g of reactant CHDA, 1.125 g of a catalyst (ruthenium-tin/carbon catalyst, comprising 5 parts by weight of ruthenium, and 5 parts by weight of tin, based on 100 parts by weight of carbon carrier), and 250 g of solvent distilled water were introduced, and purge with nitrogen of 5 bar was conducted twice, purge with hydrogen of about 5 bar was conducted twice, and then, while stirring at 50 rpm under hydrogen atmosphere (about 14-15 bar), the temperature was raised to 250° C.

After the reaction temperature was reached, hydrogen was introduced to the reaction pressure of 100 bar, and then, the stirring speed was increased to 1000 rpm and a reaction was conducted.

While conducting the hydrogenation reaction of CHDA, a solution comprising reactant and product except a solid catalyst was sampled using a sampling port, and the sampled liquid was analyzed with a gas chromatography apparatus equipped with FID (Flame Ionization Detector).

As the result of analysis, changes in CHDM yield, conversion, and selectivity according to hydrogenation reaction time were shown in FIG. 3. And, the yield, conversion, and selectivity according to time were calculated as follows, and shown in the following Table 1.

Yield=conversion×selectivity

Conversion=mole number of reacted CHDA/mole number of supplied CHDA

Selectivity=mole number of produced CHDM/mole number of reacted CHDA

TABLE 1

| | Conversion of CHDA | Selectivity for CHDM | Yield for CHDM |
|---|---|---|---|
| 1 hours | 23.6 | 24.0 | 5.7 |
| 2 hours | 89.9 | 64.6 | 58.0 |
| 3 hours | 99.2 | 92.8 | 92.1 |
| 4 hours | 99.4 | 97.3 | 96.7 |
| 5 hours | 99.3 | 98.2 | 97.5 |
| 6 hours | 99.4 | 98.3 | 97.7 |

Referring to FIG. 3 and Table 1, it can be confirmed that after a hydrogenation reaction for 6 hours, CHDM was obtained with the final yield of 97.7%, conversion of 99.4%, and selectivity of 98.3%.

And, the rate of trans CHDM confirmed by gas chromatography was about 70%, and the rate of trans CHDA before the hydrogenation step was identically maintained.

As explained, in case CHDM is prepared according to the preparation method of the present disclosure, CHDM with high trans isomer rate could be prepared with high yield.

What is claimed is:

1. A method for preparation of 1,4-cyclohexanedimethanol, comprising steps of:
    conducting a hydrogenation reaction of terephthalic acid in the presence of a first hydrogenation catalyst to prepare 1,4-cyclohexanedicarboxylic acid (CHDA) comprising cis isomers and trans isomers;
    conducting an isomerization reaction of the reaction product of the step 1 in the presence of an isomerization catalyst to isomerizes at least a part of the cis isomers of CHDA into trans isomers; and
    conducting a hydrogenation reaction of the reaction product of the step 2 in the presence of a second hydrogenation catalyst to prepare 1,4-cyclohexanedimethanol (CHDM) comprising cis isomers and trans isomers, and
    herein the reaction product the step 1 comprises cis isomers and trans isomers of CHDA at a mole ratio of 8:2 to 6:4;
    wherein the isomerization catalyst comprises monoclinic system Zirconia, and wherein the reaction product of the step 2 comprises cis isomers and trans isomers of CHDA at a mole ratio of 4:6 to 2:8.

2. The method for preparation of 1,4-cyclohexanedimethanol according to claim 1, wherein the weight ratio of the first hydrogenation catalyst and terephthalic acid is 0.01:1 to 3:1.

3. The method for preparation of 1,4-cyclohexanedimethanol according to claim 1, wherein the first hydrogenation catalyst comprises one or more metals selected from the group consisting of palladium (Pd), rhodium (Rh), ruthenium (Ru), and platinum (Pt).

4. The method for preparation of 1,4-cyclohexanedimethanol according to claim 1, wherein the first step is conducted at a pressure of 50 to 220 bar, and a temperature of 100 to 300° C.

5. The method for preparation of 1,4-cyclohexanedimethanol according to claim 1, wherein the weight ratio of the isomerization catalyst to CHDA is 0.1:1 to 5:1.

6. The method for preparation of 1,4-cyclohexanedimethanol according to claim 1, wherein the step 2 is conducted at a pressure of 20 to 200 bar, and a temperature of 100 to 300° C.

7. The method for preparation of 1,4-cyclohexanedimethanol according to claim 1, wherein, by the isomerization reaction of the step 2, among 100 mol % of the cis isomers of CHDA, 50 mol % or more are converted into trans isomers.

8. The method for preparation of 1,4-cyclohexanedimethanol according to claim 1, wherein the weight ratio of the second hydrogenation catalyst to CHDA is 0.01:1 to 3:1.

9. The method for preparation of 1,4-cyclohexanedimethanol according to claim 1, wherein the second hydrogenation catalyst comprises one or more metals selected from the group consisting of palladium (Pd), rhodium (Rh), ruthenium (Ru), and platinum (Pt), and one or more metals selected from the group consisting of tin (Sn), iron (Fe), rhenium (Re), and gallium (Ga).

10. The method for preparation of 1,4-cyclohexanedimethanol according to claim 1, wherein the step 3 is conducted at a pressure of 50 to 220 bar, and a temperature of 100 to 300° C.

11. The method for preparation of 1,4-cyclohexanedimethanol according to claim 1, wherein the reaction product of the step 3 comprises cis isomers and trans isomers of CHDM at a mole ratio of 4:6 to 2:8.

12. The method for preparation of 1,4-cyclohexanedimethanol according to claim 1, wherein the first hydrogenation catalyst comprises palladium (Pd), and the second hydrogenation catalyst comprises ruthenium (Ru) and tin (Sn).

* * * * *